United States Patent
Bapat et al.

(10) Patent No.: US 10,429,393 B2
(45) Date of Patent: Oct. 1, 2019

(54) TUMOR DECONSTRUCTION PLATFORM FOR THE ANALYSIS OF INTRA-TUMOR HETEROGENEITY

(71) Applicant: NATIONAL CENTRE FOR CELL SCIENCE, Pune, Maharashtra (IN)

(72) Inventors: Sharmila A. Bapat, Maharashtra (IN); Rutika R. Naik, Maharashtra (IN)

(73) Assignee: NATIONAL CENTRE FOR CELL SCIENCE, Pune, Maharashtra (IN)

( * ) Notice: Subject to any disclaimer, the term of this patent is extended or adjusted under 35 U.S.C. 154(b) by 200 days.

(21) Appl. No.: 15/113,000

(22) PCT Filed: Jan. 17, 2015

(86) PCT No.: PCT/IB2015/050358
§ 371 (c)(1),
(2) Date: Jul. 20, 2016

(87) PCT Pub. No.: WO2015/107499
PCT Pub. Date: Jul. 23, 2015

(65) Prior Publication Data
US 2017/0067901 A1    Mar. 9, 2017

(30) Foreign Application Priority Data
Jan. 20, 2014   (IN) ............................ 173/MUM/2014

(51) Int. Cl.
*C12Q 1/6886*    (2018.01)
*G01N 33/574*    (2006.01)
(Continued)

(52) U.S. Cl.
CPC ..... *G01N 33/57496* (2013.01); *C12Q 1/6886* (2013.01); *G01N 33/5011* (2013.01);
(Continued)

(58) Field of Classification Search
CPC ........... G01N 33/57496; G01N 33/535; G01N 33/543; G01N 33/6893; G01N 33/57484;
(Continued)

(56) References Cited

U.S. PATENT DOCUMENTS 7,115,360 B2 * 10/2006 Clarke ................. C12N 5/0695
435/4
9,470,694 B2 * 10/2016 Dertinger ........... G01N 33/5014
(Continued)

OTHER PUBLICATIONS

Hycult Biotech . Flow Cytometry. Product Description protocols (Apr. 2000)).*
(Continued)

*Primary Examiner* — Gailene Gabel
(74) *Attorney, Agent, or Firm* — Merchant & Gould P.C.

(57) ABSTRACT

The present invention provides a method for concurrent resolution of the cancer stem cell (CSC) derived hierarchy, genetic instability, differentially cycling cells and host cells recruited for performing tumor growth supporting functions; and (ii) quantification, monitoring and analysis of these populations. The first level of analysis can be carried out using either CSC- and progenitor-specific markers or a marker-free approach based on label-chase to resolve the tumor regenerative hierarchy. The next level involves combinatorial quantification of differential DNA-RNA contents to identify recruited host and tumor cell variants resulted from genetic instability and differential cycling within the tumor.

7 Claims, 5 Drawing Sheets

(51) Int. Cl.
*G01N 33/50* (2006.01)
*G01N 15/14* (2006.01)

(52) U.S. Cl.
CPC . *G01N 33/57484* (2013.01); *G01N 33/57492* (2013.01); *C12Q 2600/156* (2013.01); *G01N 15/1459* (2013.01)

(58) Field of Classification Search
CPC .............. G01N 15/1459; C12Q 1/6886; C12Q 2600/156
See application file for complete search history.

(56) References Cited

U.S. PATENT DOCUMENTS

| | | | |
|---|---|---|---|
| 2001/0000751 A1 | 5/2001 | Schmitz et al. | |
| 2010/0267079 A1 | 10/2010 | Weissman et al. | |
| 2013/0129681 A1* | 5/2013 | Covey | C12Q 1/485 424/85.7 |

OTHER PUBLICATIONS

International Search Report and Written Opinion from corresponding International Patent Application No. PCT/IB2015/050358, dated Jun. 17, 2016, 7 pages.

* cited by examiner

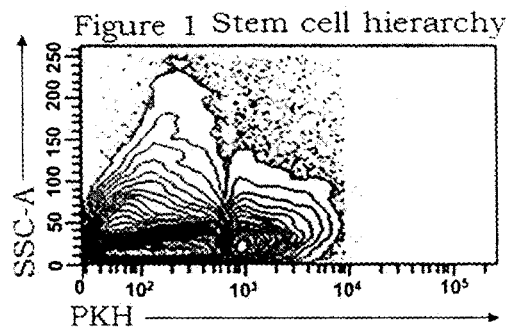
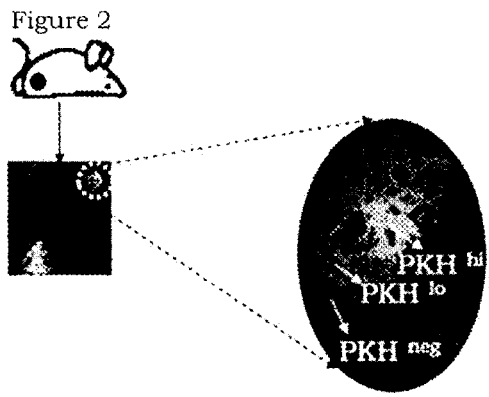
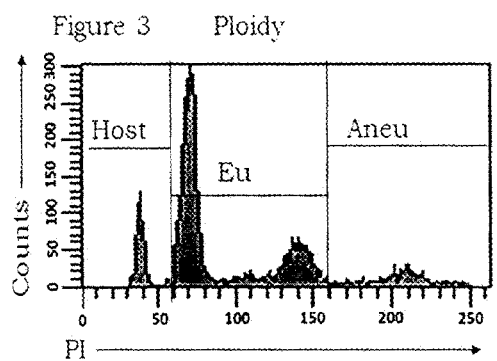
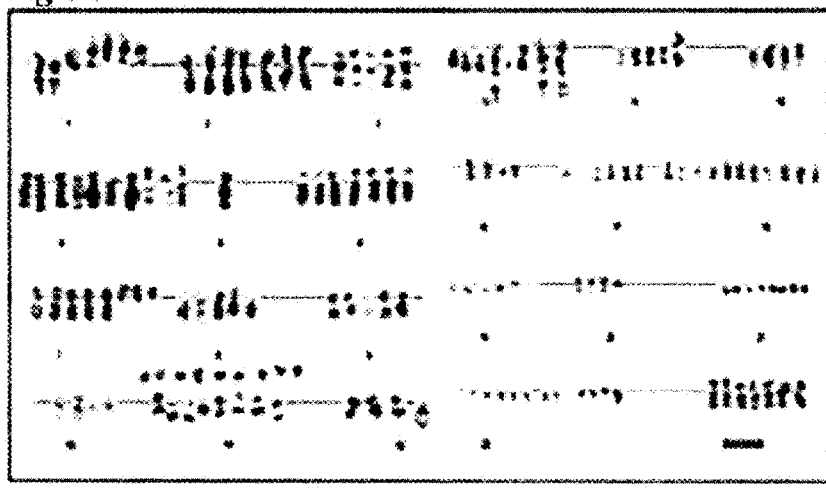

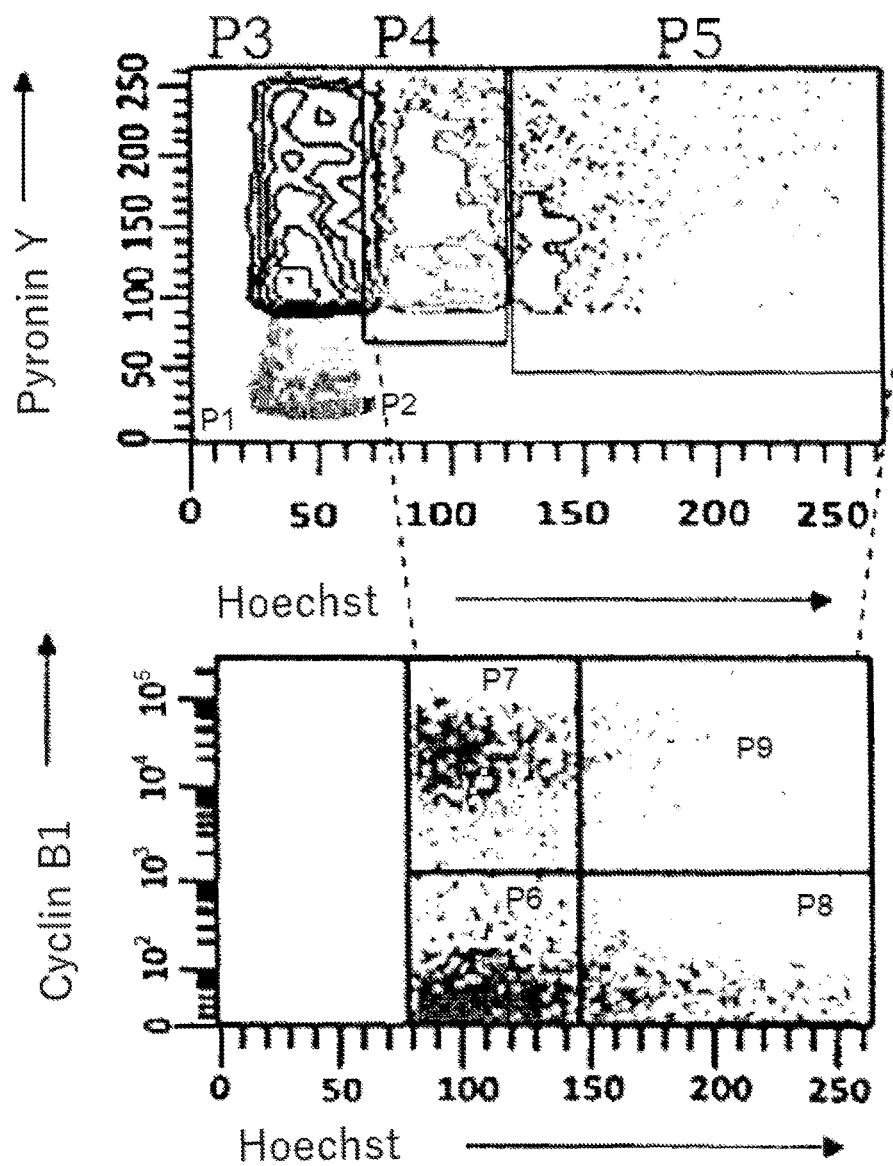
Figure 5 *Cell cycle phases*

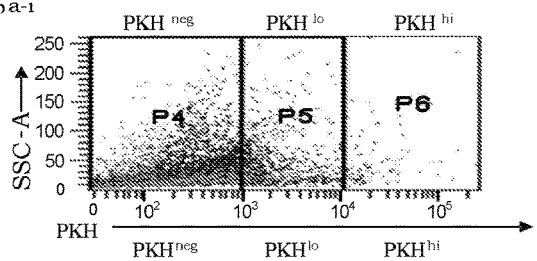
Figure 6a-i
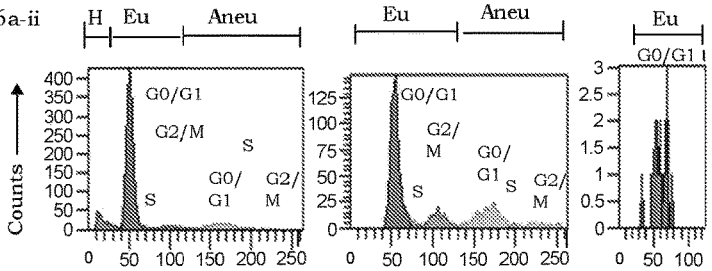
Figure 6a-ii
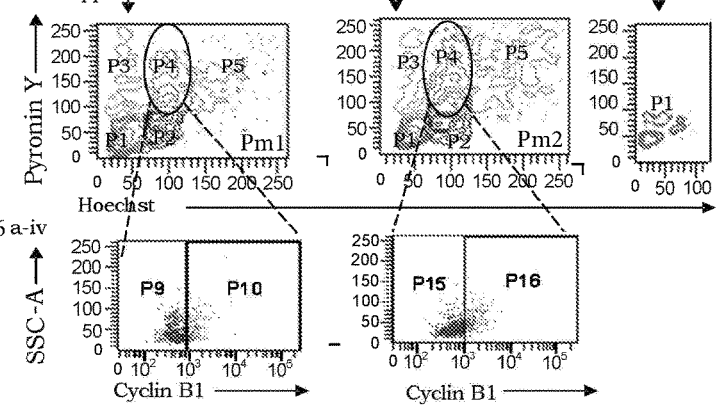
Figure 6a-iii
Figure 6a-iv
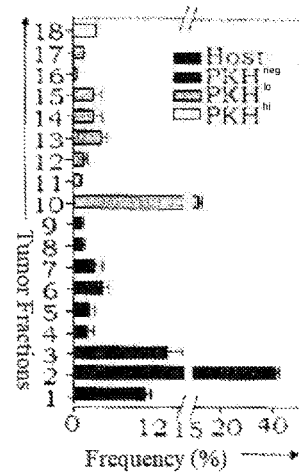
Figure 6b
1 - Host
2 - PKH$^{neg}$Eu-Go
3 - PKH$^{neg}$Eu-G1
4 - PKH$^{neg}$Eu-S
5 - PKH$^{neg}$Eu-G2M
6 - PKH$^{neg}$Aneu-G0
7 - PKH$^{neg}$Aneu-G1
8 - PKH$^{neg}$Aneu-S
9 - PKH$^{neg}$Aneu-G2M
10 – PKH$^{lo}$Eu-Go
11 - PKH$^{lo}$Eu-G1
12 - PKH$^{lo}$Eu-S
13 - PKH$^{lo}$Eu-G2/M
14 - PKH$^{lo}$Aneu-G0
15 - PKH$^{lo}$Aneu-G1
16 - PKH$^{lo}$Aneu-S
17 - PKH$^{lo}$Aneu-G2M
18 – PKH$^{hi}$Eu-G0

Figure 9

| Drugs | 1 | 2 | 3 | 4 | 5 | 6 | 7 | 8 | 9 | 10 | 11 | 12 | 13 | 14 | 15 | 16 | 17 | 18a | 18b | 18c | 18d | 18e | 18f | 18g | 18h |
|---|---|---|---|---|---|---|---|---|---|---|---|---|---|---|---|---|---|---|---|---|---|---|---|---|---|
| A | | | | | | | | | | | | | | | | | | | | | | | | | |
| B | | * | | | | | | ** | | | | | | * | * | ** | | | * | | ** | | ** | | |
| C | | ** | ** | | | * | ** | ** | ** | ** | ** | | | ** | ** | | | * | | ** | | * | | | |
| D | ** | ** | * | | ** | * | * | | * | ** | * | | ** | * | | | * | | ** | | ** | | * | | |
| E | | ** | * | | | | | * | | ** | ** | ** | | ** | * | ** | | | ** | * | ** | | * | | ** |
| F | ** | ** | ** | ** | ** | ** | ** | ** | | ** | | | | | * | * | ** | ** | | ** | | ** | | ** | ** |
| G | * | | ** | | | | | | ** | * | | | | | | ** | * | | ** | | * | | * | | * |
| H | ** | | | ** | ** | ** | | | * | * | | | | | | | | * | * | * | * | | * | * | * |
| I | * | * | * | * | * | | ** | | * | | ** | | | | ** | | | * | * | | | ** | * | * | |
| J | ** | | ** | * | * | ** | ** | ** | | * | | | | ** | ** | ** | ** | ** | ** | ** | ** | ** | ** | ** | ** |

| | |
|---|---|
| Resistant fraction | ■ |
| Sensitive fraction | ▨ |
| Maintained fraction | ▧ |
| Eliminated fraction | □ |
| P < 0.05 | * |
| P < 0.001 | ** |

TUMOR DECONSTRUCTION PLATFORM FOR THE ANALYSIS OF INTRA-TUMOR HETEROGENEITY

This application is a National Stage Application of International patent Application No. PCT/IB2015/050358, filed 17 Jan. 2015, which claims benefit of Ser. No. 173/MUM/2014, filed 20 Jan. 2014 in India and which applications are incorporated herein by reference. To the extent appropriate, a claim of priority is made to each of the above disclosed applications.

FIELD OF THE INVENTION

The present invention relates to the field of oncology and provides novel methods for identification, quantification, monitoring and analysis of intratumoral heterogeneity with respect to resolution and quantification of discrete cell sub-populations in tumors. More specifically, the major parameters of cellular components based on cancer stem cell (CSC) hierarchies; genetic instability, differential cell cycling and heterogeneity of marker expression are considered in design of an analytical pipeline preferably using flow cytometry methods. The invention will be particularly useful in the evaluation of tumor responses, especially through applications in novel target molecule/drug discovery, drug candidate screening and prediction of prognosis.

BACKGROUND OF THE INVENTION

Increased efforts in healthcare programs over the last few decades have improved the quality of human life. Cancer however, remains a leading cause of death and is considered one of the emerging 'life-style' syndromes. Unfortunately the remarkable advancements in molecular elucidation of cancer do not always translate into reliable therapeutic strategies. Radiation, chemo-, hormonal and immune therapies initially often appear to be effective in primary treatment, yet drug refractory and /or recurrent disease arising from persistent residual micrometastases often ensue and lead to adverse patient prognosis. Several unresolved issues such as late detection, failure to recognize the cellular and molecular heterogeneity of tumors, drug resistance, limitations in specific tumor cell targeting, immune evasion by tumor cells, etc. clearly necessitate development of new approaches to improve the efficacy of cancer therapy. Classically the multi-step process of mutation selection and fixing at the cellular level is established as a causative event in transformation. Activation of oncogenes through gain-of-function mutations complemented by inactivation of tumor suppressor genes by loss-of-function mutations provides a strong argument that their cognate proto-oncogenes and tumor suppressor genes normally balance positive and negative regulation of the cell cycle respectively (Coschi & Dick, 2012). Genetic insults can disrupt the cell cycle and lead to unbalanced cell proliferation; the direct correlation between increased mutational load and tumor grade has assigned a significant role for genetic instability in disease progression. Within transformed tissues, the emergence of such events is often not uniform and can generate various lineages. "Intra-tumor heterogeneity" was first realized by histopathologists as variations in morphology or staining behavior in tumors. At present it refers to the coexistence of derivatives of a transformed cell (suggestive of evolving lineages and differential regenerative capabilities), tumor-associated myoepithelial, inflammatory, immunomodulatory, endothelial, vascular and stromal components within a single tumor. At the molecular level, intratumor heterogeneity encompasses differential gene and protein regulatory networks that define cellular functions and programs.

Detection of heterogeneous behaviour can be carried out through karyotyping, spectral imaging, immunohistochemistry (IHC) based mitotic counts and total nuclear DNA content analysis (ploidy) that identify genetic instability within tumors. While H&E staining and IHC are relatively quick, inexpensive and easy techniques that have remained almost unchanged over several decades, an "all-or-none" type of analysis is impossible for most markers due to considerable intratumor heterogeneity with regard to cell compositions and levels of expression. Despite the availability of automation, manual counting is often considered more reliable, that generates possibilities of subjectivity and discordance in analysis.

Flow cytometry supports IHC through quantification of cells within a population expressing a specific marker rather than its level of expression (achieved in IHC). Such quantification is based on the assumption that the amount of fluorescent dye linearly represents the amount of marker. Profiling specific markers using single- or multi-color fluorophores is thus a well established application of flow cytometry (EP798386B1; EP2472264A3; EP741798A1). Quantification through flow cytometry of cells in S-cell cycle phase by thymidine labelling based DNA content determination is further reported to exhibit good correlation with proliferation index in histologic assessments (Cavanagh et.al. 2011). However since tumor cells also reside in other cell cycle phases, two samples with comparable S-phase fractions may exhibit different growth kinetics and responses to cycle-dependent chemotherapeutic agents. Combinations of marker profiling with cell cycle analysis and/or DNA content are also established (Corver W E et al. 1996). Thus, determination of DNA content along with specific cell cycle phase markers such as Ki-67, PCNA and/or α DNA polymerase increases the accuracy of such analysis (Tanaka et. al. 2011, Liu et.al. 2010, Crevel et.al 2012). The G0 phase however remains elusive due to lack of association with any exclusive marker; although differential DNA-RNA binding can be used to resolve this resting phase (Holyoake et al. 1999).

Application of flow cytometry using a defined panel of cell surface markers to identify cellular components of regenerative hierarchies is also robustly established for the hematopoietic system and is a routine clinical practice that supports therapeutic interventions in aberrant hematopoiesis-associated syndromes including leukaemia (Lapidot et al. 1994). Similar applications in other normal vs. aberrantly functioning adult tissues however, are not so widely established although the identification and prospective isolation of CSCs using flow cytometry or magnetic bead based sorting and application of specific markers expressed on normal stem cells has been frequently reported in the last decade (Al-Hajj et al. 2003, Singh et al. 2004, Collins et al. 2005, Li et al. 2009, Barteneva et al. Biochimica et Biophysica Acta 2013; U.S. Pat. No. 7,115,360; WO2012031280A2; US20080187938; US20080261244; U.S. Pat. Nos. 7,723,112; 8,044,259; 8,110,366). The CSC population is quite likely to be heterogeneous, as is derived from numerous reports of permutations and combinations of different markers or alternative stem cell-like functionalities such as long-term regeneration potential (Bapat et al. 2005; Smith et. al. 2011; US20130157285A1) or side-population efflux (Zhao et.al 2013) to isolate tumor fractions with comparable performances in regenerative assays. Hence, the initial expectations of possibilities from CSC identification relating to prospective isolation, characterization and investigation of crucial biological functionalities of these cells, have not really been achieved.

Marker-free identification of normal tissue stem cells and studies of their proliferation kinetics using label-chase/label quenching are earlier reported to be useful especially in tissues wherein precise marker association cannot be assigned and confirmed (Lanzkron et.al., 1999; Rousselle et al. 2001; Boutonnat et.al 2005). We had previously applied a label-chase approach to identify tumor dormancy wherein resolution of the proliferative hierarchy was derived through differential label retention, and that aneuploid cells emerging in a developing tumor contribute to drug refractory behavior (Kusumbe and Bapat, 2009a). This was the first report of application of label-chase in tumors; use of the same for CSC isolation of is in the public domain (http://www.sigmaaldrich.com/technical-documents/articles/biowire/cell-tracking-lipophilic-membrane-dyes.html) and has been used thereafter (Rainusso et. al., 2011; Ramachandran et. al., 2011; Du et. al., 2012; Ricci et. al., 2012; Wang et. al., 2012; Xue et. al., 2012; Morrison et. al. 2013; Richichi et. al., 2013). Although the study established an association of CSCs and aneuploidy with tumor dormancy, it remained a subjective observation of tumor behavior, with each parameter being studied in isolation that overlooked possible cross-regulation. Most importantly, the true tumor heterogeneity in terms of interdependent populations was not quantified. These limitations led the present invention to develop the present invention in a non-obvious manner that is useful in understanding tumor behavior, and resulted in an improved method of identification and quantification of tumour heterogeneity.

The present invention thus describes a novel method which is based on a structured population model achieved by deconstruction of tumors into discrete cell fractions mapped through concurrent analysis of regenerative hierarchies, genetic alterations and cell cycle effects in a non-obvious manner. This is a major advancement over any individual technique and achieves a higher and directed resolution of different yet relevant tumor cell types in a quantifiable manner.

OBJECTS OF THE INVENTION it is an object of the present invention to provide a method that concurrently resolves discrete cell fractions that represent the tumour regenerative hierarchy, genetic instability, differentially cycling cells and host cells recruited for performing functions that support tumor growth.

Another object of the present invention is to provide a method for quantification, monitoring and analysis of each of these subpopulations under different conditions.

Yet another object of the present invention is to provide a method for definitive screening of markers and drugs thereby leading to identification of new drug targets.

it is yet another object of the present invention to provide a method for identification, quantification, monitoring and analysis of intra-tumor heterogeneity, a definitive approach for drug repositioning through generating possibilities of novel drug combinations involving with new and/or known compounds that can repurposed in a targeted manner.

SUMMARY OF THE INVENTION

In one aspect the present invention provides a method for identification, quantification, monitoring and analysis of cellular heterogeneity in tumours, wherein said method comprises the steps of:

obtaining a sample of tumour-derived single cell suspension, wherein said sample is from established cell lines or primary tumor samples.
  (ii) fixing and permeabilizing said tumour-derived single cell suspension
  (iii) staining or labelling said tumour-derived single cell suspension with a binding dye or a flurophore or antibodies;
  (iv) concurrently resolving said labelled tumour-derived single cell suspension through flow cytometry or fluorescence activated cell sorters to three levels of resolution of its cellular components;
  (v) detecting the frequency and identifying the profile of said levels of resolution;
  (vi) subjecting said frequency and profile to combinatorial analyses, wherein the first level of resolution is based on tumour proliferative or regenerative hierarchy; the second level is based on varying DNA content; and the third level is based on cell cycle phases.

In another aspect the present invention provides a method for screening of markers associated with specific populations or functions, novel drugs, drug targets, towards applications in drug repositioning in a cell-specific manner.

In yet another aspect the present invention provides a method wherein the first level of resolution of a tumor regenerative hierarchy is through chasing quenching dynamics of vital membrane fluorophores (VMF).

In a further aspect, the present invention provides a method wherein the second level resolution is based on differential quantification of cellular DNA-RNA content and cell cycle phases that resolves the host and tumor cell-derived populations, and further those with varying ploidy levels (genetic instability) and differential cycling within the tumor.

In yet another aspect the present invention provides a method wherein the third level of resolution is based on the G0 and G1 cell cycle phases and is achieved by combinatorial staining of the TDSCS with DNA and RNA binding dyes (such as Hoechst and Pyronin Y respectively) prior to flow cytometry, in which the RNA binding dye can be replaced with antibodies recognizing markers such as Ki67 or PCNA that are expressed in G1 but not G0 cell cycle phases.

In yet another aspect, the present invention provides a method for quantification, monitoring and analysis of each of these subpopulations under different conditions and can be applied to study patterns of evolution during tumor progression or under conditions of stress.

In yet another aspect the present invention provides a method of screening of markers across these subpopulations to define expression profiles and new drug targets in a cell-specific manner.

In yet another aspect, the present invention provides a method for screening of novel drug candidates through evaluation of their responses in modulating intra-tumor heterogeneity within post-treatment residual tumors.

In yet another aspect the present invention provides a method for drug repositioning through generating possibilities of novel drug combinations involving with new and/or known compounds that could be rescued and repurposed in a targeted manner.

BRIEF DESCRIPTION OF THE ACCOMPANYING DRAWINGS

FIG. 1 shows a representative FACs profile of the three PKH intensity based subsets namely PKH$^{hi}$, PKH$^{lo}$, PKH$^{neg}$ wherein PKHhi represents the dye retaining fraction, $PKH^{lo}$ fraction undergoes partial dye depletion and PKHneg fraction shows complete dye depletion.

FIG. 2 shows a cryosection of A4 PKH67 labeled xenograft tumor wherein PKH67 is detected as green fluorescence and nuclei stained with propidium iodide (PI) appear red in color; inset indicates the three PKH intensity based cellular subsets.

FIG. 3 shows representative PI staining-based ploidy fractions including the host, euploid (Eu) and aneuploid (Aneu) cell populations.

FIG. 4 shows one representative aneuploidy associated karyotype.

The upper panel in FIG. 5 represents resolution of DNA-RNA content (Hoechst-PyroninY staining)—based fractions (P1-EuG0; P2-AneuG0; P3-EuG1; P4-EuSG2M+AneuG1; P5-AneuSG2M), while the lower panel indicates further resolution of mixed P4 into P6-AneuG1S & P7-EuG2M and P5 into P8-AneuS+H-AneuG1 & P9-AneuG2M through Cyclin B1(G2 phase) staining.

FIG. 6a-i. Representative FACs profile of PKH staining of A4 xenograft; 6a-ii. Representative FACs profile of PI staining for ploidy states and cell cycle phases of PKH derived subsets of A4 tumor; 6a-iii. Upper panel- Representative FACs profile of Hoechst-PyroninY staining of PKH derived subsets where (P1-EuGO; P2-AneuGO; P3-EuGl; P4-EuSG2M+AneuGl; P5-AneuSG2M); 6a-iii. Lower panel - Resolution of G2/M phase by Cyclin B1staining of P4 (mixed fractions) of PKH derived subsets stained by Hoechst pyronin Y where P9- PKHneg Aneu G1, P10 - $PKH^{neg}$ Eu-G2/M, P15-$PKH^{lo}$ Aneu-G1, P16-PKHlo Eu-G2/M; 6b. Frequency of 18 A4 tumor fractions (±SEM) based on combined FACs analysis of proliferative hierarchy, ploidy and cell cycle phases.

Figure 7:
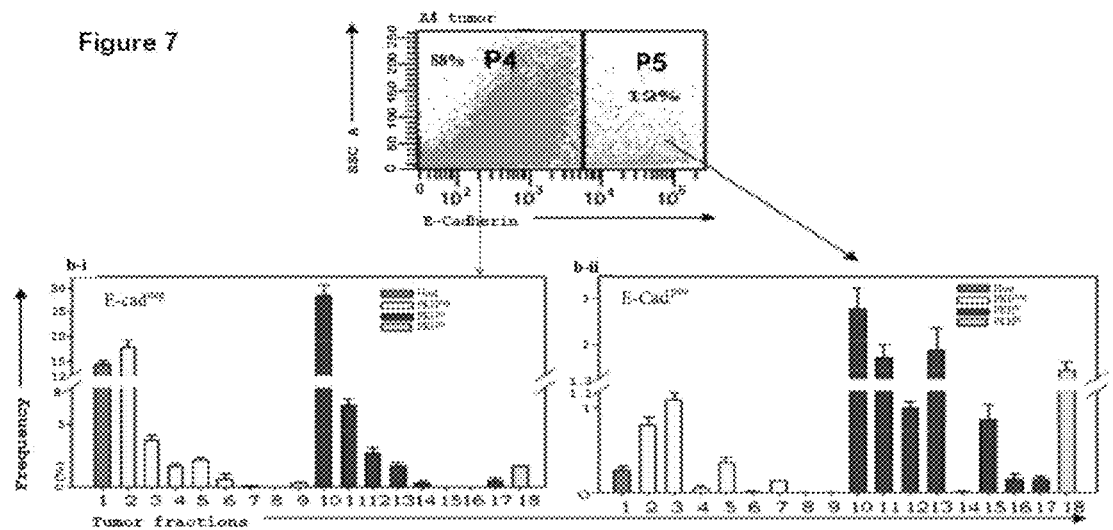

FIG. 7a is a representative FACs image of E-cadherin expression as detailed in Example 2; b-i & b-ii. Graphical representation of frequency of $E-cad^{pos}$ and $E-cad^{neg}$ cells across the 18 tumor cell fractions, wherein populations 1-18 are as depicted in FIG. 6b; *–P<0.05; –P<0.001; *–P<0.0001.

Figure 8:
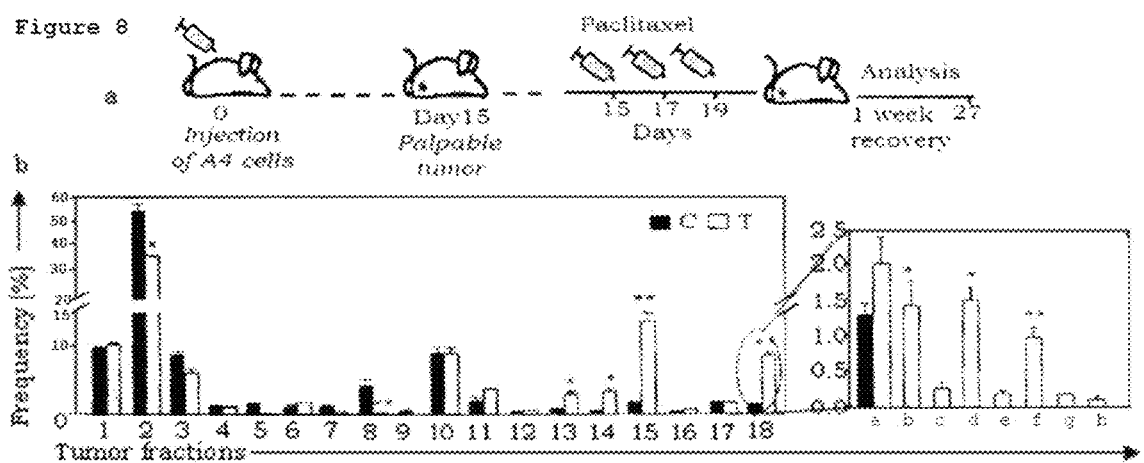

FIG. 8 represents data discussed in Example 3. a. Schematic of paclitaxel administration regime; b. Frequency (±SEM) of tumor fractions based on proliferative hierarchy, ploidy and cell cycle analysis in control and paclitaxel treated where populations 1-18 are as depicted in FIG. 6b, inset indicates frequency of cycling CSCs, 18a-$PKH^{hi}$ Eu G0, 18b-$PKH^{hi}$ Eu G1,18c-$PKH^{hi}$ Eu S, 18d-$PKH^{hi}$ Eu G2/M, 18e-$PKW^{hi}$ Aneu G0, 18f-$PKH^{hi}$ Aneu G1, 18g-$PKH^{hi}$Aneu S, 18h-$PKW^{hi}$ Aneu G2/M;*–P<0.05; –P<0.001; *–P<0.0001.

FIG. 9 represents the efficacy of various drug regimes through resolution of residual tumor composition after therapy in comparison with a naïve (untreated) tumor for following drug regimes—Pac ST (paclitaxel short-term: 3 doses—48 h intervals—1 week recovery), Pac LT (paclitaxel long-term, 2 cycles of ST regime); Gem ST (gemcitabine short-term, 3 doses—36 h intervals—36 h recovery), Gem LT (gemcitabine long-term, 5 doses—36 h intervals—36 h recovery); 5AzadC (3 doses—48 h intervals—1 week recovery); mAbX (6 doses of an uncharacterised antibody developed in the Bapat lab—48 h intervals—48 h recovery); Gem+mAbX ST combination therapy (3 doses of each drug—48 h intervals—48 h recovery), Gem+mAbX LT combination therapy (2 cycles each comprising of 3 doses of each drug—48 h intervals—1 week recovery); triple drug combination of gemcitabine, mAbX and 5AzadC LT (6 therapeutic cycles, each comprising of 3 doses of each drug at 48 h intervals and 1 week recovery); populations 1-18 and 18a-18h are as defined in FIGS. 6b and 8 respectively.

DETAILED DESCRIPTION OF THE INVENTION

The present invention relates to methods in the field of oncology. In particular it relates to a method for identification, quantification, monitoring and analysis of cellular heterogeneity in tumors by way of three levels of resolutions, namely, tumor proliferative/regenerative hierarchy, DNA content and the stage of cell division.

There has always been an interest in finding procedures using experimental models of tumor growth that mimic human disease towards the address of specific issues in cancer research besides improving patient diagnosis and prognosis. The present invention also relates to a mechanism for evaluating such efficacies thereby making it an indispensable tool for targeted drug development.

The sample can be from cells lines such as ovarian cancer (A4, OVCAR3), teratocarcinoma (NT2), colon cancer (HT29), prostate (PC3, DU145), cervical cancer (ME180), kidney cancer (ACHN), lung cancer (A549), skin cancer (A431), glioma (C6), but are not limited to only these lines.

In the present invention, population resolution and enumeration assays are used at different levels. At the first level, the regenerative tumor hierarchy is identified through label-chase based on the premise that label dilution is a derivative of the number of cell divisions undertaken by a cell.

The gradient of proliferative potential based on label-chase correlates with components of the hierarchy that are identified as three major tumor subsets viz. $VMF^{hi}$, $VMF^{lo}$ and $VMF^{neg}$, wherein $VMF^{hi}$ represents quiescent label retaining cells most likely to be CSCs, $VMF^{lo}$ represents cells that have undergone partial label dilution including progenitors and cell cycle arrested cells, and $VMF^{neg}$ represents differentiated cells which have undergone total label quenching.

Secondly, identification of the supporting host populations and genetically unstable cells based on their differential DNA content within the each components of the regenerative tumor hierarchy in tumor xenografts is achieved. It involves staining of the TDSCS with a DNA binding dye such propidium iodide (PI) prior to flow cytometry first resolves three different fractions varying in their DNA content and cell cycle phases as—host (DNA content equal to '2n' content of the experimental animal host), euploid (DNA content equal to '2n' content of xenografted tumor cells) and aneuploid (DNA content more than '2n' content of xenografted tumor cells). Where the DNA binding dye used is PI, three cell cycle phases viz. G0-G1, S and G2/M can also be identified within each of these fractions.

The last level involves resolution and enumeration of the cell cycling phase, genetically stable and unstable cell populations across the regenerative tumor hierarchy. Within the profiles obtained by way of the above two levels of resolution, a mixed Euploid SG2M+Aneuploid G1 fraction is obtained and can additionally be further resolved by staining in combination with immunophenotyping with antibodies recognizing a marker such as Cyclin B1 that is expressed in the G2-M cell cycle phase.

Variations in the frequencies and profiles of these populations are exist in different xenografts from different tumors/cell lines depending on the tissue of origin, tumor class, and background of the host animal, conditions during xenograft development, besides other biological and clinical parameters; all of these can be attributed to inter-tumor heterogeneity. Thereby combinatorial differential quantification of cellular DNA content (ploidy, genetic instability), differential cycling, and resolution of G0/G1 phases and mixed Euploid SG2M+Aneuploid G1 fractions within the tumor are achieved. Cell cycling heterogeneity also accounts for heterogeneity in expression of some proteins, transient drug resistance and tumor dormancy or minimal residual disease associated with tumor recurrence.

Raising Xenografted Tumors and Flow Parameters

Xenograft models are important for simulating disease parameters that permit testing methods of treating a live subject. Current tumor xenograft models often use immunodeficient mice for assessing drug, radiation and combination(s) of drugs and radiation efficacy. For simulating the disease parameters, the xenograft comprises of human tumor tissue derived cells selected from the group consisting of breast, ovarian, lung, prostate, colon, renal, liver, skin leukemia, lymphoma, etc. Alternatively, cell lines established from human tumors can also be used to generate xenografts.

Methods for the Resolution of the Regenerative Tumor Hierarchy

The present invention provides many advantages through the use of label-chase to identify a regenerative tumor hierarchy in xenograft tumors generated from VMF-tagged cells. Consequent to each cell division, the VMF is equally distributed between the two daughter cells. Thereby, based on the extent of label quenching in the tumor, three different fractions referred to as $VMF^{hi}$, $VMF^{lo}$ and $VMF^{neg}$ fractions can be identified within the TDSCS using a flow cytometer to effectively define the tumor-associated proliferative heterogeneity. The $VMF^{hi}$ fraction is likely to capture all CSC stem cell clones/subsets that may exhibit genotypic, phenotypic and functional heterogeneity (including all immunophenotypes, expression of dye efflux properties, differential quiescence, regenerative capabilities, etc.). The $VMF^{lo}$ fraction includes progenitor cells and those that undergo cell cycle arrest after 4-5 population doublings. The $VMF^{neg}$ fraction comprises cells resulting from several population doublings, as well as those recruited from the host.

FIG. 1 exemplifies PKH26 as the VMF used in generating xenografts. Most importantly, the techniques provided by the present invention for detecting and resolving such a hierarchy are easy to use and have a high level of reproducibility, in contrast to the complex phenotypes defined by multiple surface markers and/or other biochemical and molecular parameters. Unlike certain functional assays such as exclusion of dyes that bind to nucleic acids, methods of the present invention are also non-toxic for tumor cells. Although in most of the preferred embodiments, the hierarchies are of human origin, they are not intended to be limited thereto.

In one embodiment, all CSCs that are associated with different features can be identified as $VMF^{hi}$ cells viz. those that undergo minimal label quenching, retain the same intensity levels as those at the time of xenograft initiation and survive under in vivo conditions at least till the xenograft is established and harvested. This length of time usually ensures that most of the other non-dividing cells besides the quiescent CSCs in a cell mixture implanted for xenograft initiation are depleted by the time of tumor harvest. Thereby the invention provides a commonality for detection of all CSC variants within tumors. CSCs are defined and functionally characterized as a small subset of cells from a tumor that have self-renewal capabilities (indefinite growth in vitro under appropriate conditions and ability to generate tumors in vivo from a few number of cells). In the present invention, cells that retain the label at the same levels as at the time of xenograft initiation and which survive within the experimental in vivo conditions at least till the xenograft is established and retain the properties of reversible quiescence, self-renewal and regeneration, are considered as CSCs. Further combining label-chase with the individual detection methods of each CSC type may be pursued for addressing specific biological queries relating to individually defined sub-populations.

In another embodiment, the next level of the tumor regenerative hierarchy, viz. tumor progenitors is very effectively resolved through label-chase as $VMF^{lo}$ cells that, like the $VMF^{hi}$ fraction include all varied cell types within the group. This is an important advancement in the field in which the current emphasis on CSC identification and their characterization has overshadowed realization of the crucial involvement of progenitor cells in tumor maintenance and propagation of disease. Progenitors constitute the 'workhorse' in a regenerative tumor hierarchy and through their highly proliferative capabilities, generate the requisite critical mass of cells that will undergo differentiation along specific lineages characteristic of the tumor histotype. In the specific context of tumor hierarchies, a fraction of these could be 'maturation arrested' resulting in blast crises, in which progenitors retain their proliferative capabilities, but cannot give rise to functional, terminally differentiated cells. Further, combining label-chase with immunophenotyping methods using progenitor 'markers' may be applied for addressing specific biological queries.

$VMF^{neg}$ cells do not express any label intensity, which in most cases constitute the large bulk of a tumor. This is a highly heterogenous population that includes different host cell types recruited for supporting tumor growth as well as components of various differentiation lineages derived from the proliferative tumor progenitors. The physical, biochemical and molecular pattern of differentiation of these cells are important histologic parameters that impart a distinct tumor identity. Combination of label-chase with immunophenotyping methods using specific cell surface markers may be used for further elucidation of different cell types within this fraction.

In a particular embodiment, differential label retention can be visualized in situ within cryosections that are observed under the microscope (FIGS. 1 and 2 exemplify PKH67 as the VMF used in generating xenografts), with considerable correlation between differential label retention capabilities of the populations detected in such cryosections and those through flow analysis.

Methods for Identification of Host Contribution and Genetic Instability Through Resolution of Differential DNA Containing Tumor Populations The second level of resolution involves staining of an aliquot of the TDSCS with DNA binding dyes such as Hoechst or propidium iodide (PI) before flow cytometry and FACs data acquisition. FIG. 3 represents the profiles of three discrete populations demarcated based on their varying DNA content as below (i) xenografted euploid cells (2n-4n) wherein euploid DNA content is equivalent to the DNA content of the tumor cells grown in vitro and is associated with a specific modal chromosome number (MCN), (ii) aneuploid derivatives of xenografted cells (>two times euploid DNA content of tumor cells), and (iii) Host (mouse) derived cells DNA content <euploid DNA content. Further karyotype analysis of the aneuploid fractions revealed highly variable chromosome numbers as represented in FIG. 4 and affirmed that increased DNA content did not result from artifacts, data acquisition or analytical errors.

Methods for the Resolution of Differential Cell Cycling Populations

Profiling the intensity of staining by DNA binding dyes as above has an additional advantage of revealing the basic cell cycle phases viz. G0/G1, S and G2/M (as represented in FIG. 3) that provides information regarding the proliferative capability of a tumor. The invention demarcates five cell fractions viz. P1 (euploid G0), P2 (aneuploid G0), P3 (euploid G1), P4 (mixed euploid SG2M and aneuploid G1S) and P5 (aneuploid SG2M) in xenografted tumors as represented in the upper panel of FIG. 5. The third level of resolution involves—

(i) Additional staining of TDSCS for estimating combinatorial DNA and RNA content using specific binding dyes, or (ii) Combining DNA content estimation with immunophenotyping for a G1 cell cycle marker which may be either but not limited to Ki-67 or PCNA.

Computation of results from both, PI-and G0/G1 resolution-based cell cycle profiles leads to enumeration of tumor cells in each cell cycle phase. However, since tumors are genetically complex and heterogeneous mixture of cells, overlap between increased DNA content resulting from genetic instability versus intracellular DNA synthesis as a part of cell cycle progression, can lead to erroneous computation. The present invention addresses this by concurrently resolving the mixed cell population. Particularly as represented as P4 in FIG. 5 by combining DNA content estimation and G0/G1 resolution of cell cycle phases with additional immunophenotyping of cells for expression of either a G1 or G2M phase marker which could be but is not limited to Cyclin B1.

The above embodiments defined for each level of resolution viz. tumor regenerative hierarchy, host contribution & genetic instability, and differentially cycling tumor cells contribute to the actual identification of a minimum number of discrete cell populations associated with intrinsically different capabilities.

Methods for Combinatorial Analysis

The present invention further provides combinatorial analysis based on the frequencies and profiles generated from the above discussed levels of resolution. These results are subjected to rigorous analysis to identify and enumerate and mathematically compute the variants generated from different permutations and combinations of the above biological parameters. The methods presented here are only illustrative and not limited to the analysis indicated below. A variant scheme for example, could be designed to change the sequence of overlap of the three different levels and focus on some of the populations and mask yet other(s) deemed to be unnecessary in a specific experimental set-up.

(a) Combinatorial Analysis of Two Levels—Regenerative Hierarchy and DNA Content

An overlap of the profiles of these two levels of resolution computes frequencies of the following sub-fractions in established xenografts—

(i) $VMF^{neg}$ cells comprise of host, euploid and aneuploid sub-fractions, (ii) $VMF^{hi}$ cells include euploid and aneuploid sub-fractions, and (iii) $VMF^{hi}$ cells appear to be almost entirely euploid—which may be due to their infrequent cycling that decreases the possibility of generating genetic rearrangements.

(b) Combinatorial Analysis of all Three Levels—Regenerative Hierarchy, DNA Content and Cell Cycle Status A consolidated analysis of various cell groups resolved at each level as defined by the embodiments of the present invention compute frequencies of the following discrete cell groups in established xenograft tumors tagged with any VMF as—

(i) $VMF^{neg}$ cells include host, $VMF^{neg}$ Euploid G0, $VMF^{neg}$ Euploid G1, $VMF^{neg}$ Euploid S, $VMF^{neg}$ Euploid G2/M, $VMF^{neg}$ Aneuploid G0, $VMF^{neg}$ Aneuploid G1, $VMF^{neg}$ Aneuploid S and $VMF^{neg}$ Aneuploid G2/M.

(ii) $VMF^{lo}$ cells include $VMF^{lo}$ Euploid G0, $VMF^{lo}$ Euploid G1, $VMF^{lo}$ Euploid S, $VMF^{lo}$ Euploid G2/M, $VMF^{lo}$ Aneuploid G0, $VMF^{lo}$ Aneuploid G1, $VMF^{lo}$ Aneuploid S and $VMF^{lo}$ Aneuploid G2/M.

(iii) $VMF^{hi}$ cells include $VMF^{hi}$ Euploid G0, $VMF^{hi}$ Euploid G1, $VMF^{hi}$ Euploid S, $VMF^{hi}$ Euploid G2/M, $VMF^{hi}$ Aneuploid G0, $VMF^{hi}$ Aneuploid G1, $VMF^{hi}$ Aneuploid S and $VMF^{hi}$ Aneuploid G2/M.

By applying the embodiments of the invention, discrete cell populations derived from the host cells, regenerative tumor hierarchy, genetically unstable cell lineages that exhibit differential cycling parameters can thus be profiled, enumerated and sorted as per experimental requirements. It will be appreciated that xenografts developed from any mammalian solid tumor or cell line can be resolved to identify the extent of tumor heterogeneity using the methods of the invention as outlined.

The present invention provides for an in-depth analysis through extensive data generated through flow cytometry, and which culminates in a deep mechanistic understanding and interpretation of cancer biology and its multiple facets.

Evaluation of Therapeutic Efficacy Towards Prediction of Patient Responses

Currently risk assessment in cancer, early detection, prevention, prognostication, drug efficacy and overall patient survival is being realized to ultimately hinge on intratumor heterogeneity. Studies on evaluation of therapeutic efficacies within solid tumors suggest selection of optimal therapeutic regimens for patients through characterizing intratumor heterogeneity to arrive at a precise quantification of tumor composition. The present invention can be employed to evaluate drug efficacy, and includes identification of —

(i) reversible quiescence of CSCs, an elusive phenomenon that is more hypothetical than actually demonstrated and is believed to give rise to recurrent disease. CSCs are intrinsically more aggressive that other tumor cells with their stem cells properties of quiescence, higher regeneration potential and resistance to stresses including radio- and chemo-resistance, (ii) reversible growth arrest of tumor cells with or without genetic rearrangements that permit survival and/or stress-resistant growth under adverse conditions, (iii) de-differentiation of tumor cells to acquire 'stemness' features, (iv) expression of molecules/pathways that impart resistance to drugs, (v) cross-talk with the tumor microenvironment that enhances the resilience and dissemination of tumor cells.

The uncertainty of drug resistance, tumor dormancy and minimal residual disease that remains undetected by routine methods, yet threatens to lash out recurrent, aggressive disease is a grim reality faced by most cancer patients. The combined resolution of a tumor regenerative hierarchy, genetic instability, cycling status of tumor cells and host-derived influences in the present invention is used for predicting the response of an individual to a specific therapy.

Integration in the Drug Discovery, Screening and Repurposing Pipeline

Most established drug screening assays provide limited information about the molecular and cellular specificity of drug candidates, and none regarding the composition and functionality of residual tumor cells. This arises from the fact that at present, few cellular subsets can be precisely resolved and identified within a tumor. The invention described herein provides improved methods for drastically enhancing the current drug discovery process through prediction of residual regenerative potential in xenograft tumors (cell line- or patient-derived) following exposure to known/novel drugs or drug candidates. Evaluation of perturbed frequencies of CSCs, progenitors, differentiated cells, genetically instable, cycling populations and host-derived cells in drug naïve versus treated xenografts can be compared to identify modulation of each cell fraction that reflects on its specific response to the test compound. This information on the interaction of a test compound with a specific cell population that responds by surviving or undergoing apoptosis in the presence of the drug (positive or negative drug selection) would make it possible to determine direct cell targets. Towards affirming of effects, sorted individual cell fractions can be further subjected to standard functional assays such those for self-renewal and regeneration. Such information is immensely valuable and makes this invention useful in the high throughput drug screening pipeline at present. Resolution of the crucial factors as discussed hereinabove, provides a direction to probe the interpretation of perturbation patterns.

In a further application, combining for expression of markers such as molecular targets of the drug (if known), or generic markers associated with cellular states of resistance, cell death, senescence etc. can be integrated in the discovery process to associate response with possible drug mechanisms to provide further understanding of candidate drug efficacy and its applications. A single dose of any compound to be tested as a chemotherapeutic drug leads to a change in the spatial dynamics of tumor cells through specific targeting of certain cell types, altered cell membrane and cycling properties, redistribution of available tissue nutrients and oxygen, and realignment of supporting tumor matrices that alters the cell-niche mediated cross-talks and regulation. Integration with an additional step of profiling direct/specific cellular targets of the drug(s) or known mechanisms of action would further identify other compounds having similar/more specific/complementary effects. Such targeted integration provides a value-addition in the in development of effective combinatorial therapeutic strategies.

Applications to Novel Marker (Diagnostic, Prognostic and Predictive) and Drug Target Identification Based on the transcriptional, translational and biological state embodiments, it becomes possible to develop newer approaches in applying the present invention towards identification of novel markers and drug targets. For example, it may be of interest to identify mechanisms by which a drug is specifically effective against either of the CSC, genetically unstable, aneuploid, angiogenic cells within the tumor. A concerted study of the above three states in different cell populations will thus assign a deeper meaning to drug evaluation through a precise understanding of the pathways targeted based on a systems analysis of direct and indirect/secondary target networks in a cell-specific manner to mediate targeted biological efficacy. Further, such evaluation can yield relevant information towards the development of diagnostic, prognostic and predictive marker identification that could be significant either by itself, or complement newly identified drug target profiling.

EXAMPLES

The following EXAMPLES are presented in order to more fully illustrate the preferred embodiments of the invention. The examples focus on the analysis on xenograft tumors generated from a high-grade serous ovarian adenocarcinoma cell line established earlier (A4 cell line—Bapat et al. 2005). It should be appreciated that there are several variations contemplated within the skill in the art, and that the EXAMPLES are not to be construed as limiting the scope of the invention, or any theory or suggested mechanism(s) as defined or predicted by the appended claims and embodiments.

Example 1

Preparation of Xenografted Tumors and Flow Parameters

Standard techniques are used in the process that is illustrative rather than limiting; other common methods are acceptable in the practice of this invention. Tumor tissues were rinsed several times with phosphate buffered saline (PBS) containing antibiotic and/or anti-fungal agents, finely minced and suspended in basal media supplemented with cell dissociation agent(s) with intermittent pipetting to loosen cell aggregates. Various combinations of dissociation agents can be used depending on the tumor type and appearance and including but not being limited to EDTA, EGTA, cocktails of enzymes including trypsin, dispases, collagenases, DNAse, and the like. On dispersion of tumor cell aggregates, enzymatic activity is usually terminated by addition of serum, cells pelleted by centrifugation and washed several times with basal medium and filtered through cell strainers to obtain a single cell suspension. Cell lines are harvested as per established guidelines to obtain a single cell suspension. Single cells are labeled with vital membrane fluorophore dyes (VMF) as per the manufacturer's instructions; current popular VMFs include PKH, CFSE, CellVue, Vybrant or any dye that does not affect cell viability and is chemically stable for at least 10 weeks in xenografts. Labeled cells are xenografted in immunocompromised mice, which could be either nude, SCID, Beige/SCID, NOD/SCID, Rag-/Rag-, humanised mice models, or any known experimental xenograft animal model. Control tumors were concurrently generated using unlabeled cells. Xenografts were harvested as per animal experimental protocols and digested to generate single cell suspension from which the different sub-populations were resolved through flow cytometry.

Basic cell parameters FSC and SSC were adjusted with ND filter 1.5/2 with appropriate FSC and SSC thresholds. Cell debris was eliminated based on low FSC—low SSC, doublets using Area—width parameters and RBCs based on nuclear Propidium iodide (PI) staining. PI excitation/emission maxima are at 535/617 nm (PE channel of blue laser used for analysis). Freshly labeled cells are used to set the gates for $VMF^{hi}$ cells, while TDSCS from unlabeled tumors was used in order to set the gates for $VMF^{neg}$ cells. Other fluorophores including Hoechst (UV laser), Pyronin Y (PE channel of blue laser), APC (red laser) and others can be incorporated into this scheme based on their compatibility and resolution capabilities of the flow equipment used for data acquisition and/or sorting as per experimental requirements.

FIG. 1 exemplifies PKH26 as the VMF used in generating xenografts. Work conducted during the development of the present invention using xenograft models and analysis demonstrated that the $VMF^{hi}$ population represents 0.1-18% of the tumor samples, $VMF^{lo}$ fraction that undergoes partial label quenching ranges from 22-77%, while the $VMF^{neg}$ that comprises cells associated with total label quenching and those recruited from the host cells constitutes 11-77% of the total xenograft.

Profiling the intensity of staining by DNA binding dyes as above has an additional advantage of revealing the basic cell cycle phases viz. G0/G1, S and G2/M (as illustrated in FIG. 3) provides information regarding the proliferative capability of a tumor. The third level of resolution involves (iii) Additional staining of TDSCS for estimating combinatorial DNA and RNA content using specific binding dyes Hoechst (DNA) and Pyronin Y (RNA) respectively. At G0, cells contain minimal amount of RNA and hence are demarcated as those staining poorly with Pyronin Y. For this, an aliquot of TDSCS is fixed and permeabilized using standard protocols followed by staining with Hoechst (1-10 µg/ml for 30-60 minutes) and Pyronin Y (0.1-5 µg/ml for 30-60 minutes) at 37° C.

(iv) Combining DNA content estimation with immunophenotyping for a G1 cell cycle marker which may be either but not limited to Ki-67 or PCNA. Fixed, permealized TDSCS is immunophenotyped with Ki-67 or PCNA primary antibody for 30-60 minutes at ambient temperature, washed twice with buffer and subsequently incubated for 30-60 minutes with a secondary fluorophore tagged antibody that is compatible with the VMF and DNA binding dye. Staining can also be performed with Ki-67 or PCNA antibody directly tagged by a compatible fluorophore.

An additional TDSCS aliquot was fixed and permeabilized using standard protocols, Cyclin B1 primary antibody allowed to bind to cells for 30-45 minutes, washed twice with 1× PBS and subsequently incubated with a secondary fluorophore tagged antibody that is compatible with the VMF, DNA—RNA binding dyes or DNA binding—G1 detection as per the above scheme. Staining can also be performed with compatible fluorophore direct tagged Cyclin B1 antibody. Thereby, euploid SG2M populations P6 and aneuploid G1S populations P7 & P9 respectively were identified as represented in upper panel of FIG. 5. P8 is likely to be a hyper aneuploid population in the tumor.

Example 2

Profiling of a Specific Marker Across Tumor Cell Sub-Populations

The purpose of this example is to demonstrate a specific instance of profiling a cell-adhesion molecule E-cadherin (E-cad), an epithelial marker known to be associated with transformation, invasion and metastases (Niessen et. al, 2011) that enhances the understanding of a specific cellular state or functionalities of specific cells or cell groups within a tumor. Generation of A4 serous ovarian adenocarcinoma xenografts, TDSCS, data acquisition and analysis to identify 18 discrete tumor cell populations was carried out as described above, except for additionally staining the TDSCS with commercial anti-E-cad antibody prior to profiling for data acquisition and analysis.

While a large fraction of A4 serous ovarian adenocarcinoma cells cultured in vitro exhibits high E-cadherin expression (Bapat et al. 2005), this frequency was reversed in xenografts with $E\text{-}cad^{pos}$ cells comprising around 12% and the remaining being $E\text{-}cad^{neg}$ (FIG. 7a). Almost all the recruited host cells (population 1, red bars) lack E-cad expression, possibly since it comprises of host derived stroma, vasculature and immune cells (FIG. 7b-i, b-ii); the few cells within this fraction that express E-cad are possibly derived from myoepithelial cells. Similarly, a majority of the $E\text{-}cad^{neg}$ cells are euploid and appear to be slow-cycling (populations 3,4,5 & 11,12,13), while $E\text{-}cad^{pos}$ cells in $PKH^{neg}$ euploid, $PKH^{lo}$ euploid and aneuploid fractions are suggested to be rapid cycling. The frequency of $E\text{-}cad^{pos}$ cells in the quiescent $PKH^{hi}$ fraction (population 18) is significantly high. Thereby, the most striking difference between $E\text{-}cad^{neg}$ and $E\text{-}cad^{pos}$ cells in the $PKH^{neg}$ and $PKH^{lo}$ fractions appears to be their cycling status. This actually suggests that E-cad expression could be associated with cycling progenitors, aneuploid cells and a fraction of CSCs. More importantly, such molecular profiling reveals the diversity within the CSC and progenitor fractions vis-à-vis cycling in correlation with specific marker expression. In a similar manner, profiling of any molecular marker across 18 tumor cell populations can be carried out as is claimed towards enhancing the resolution of molecular mechanisms understanding marker regulation and functions in situ. FIG. 6 exemplifies this analysis using PKH67 as the VMF.

Example 3

Prediction of Therapy Outcomes Through Modulation of 18 Tumor Subsets on Exposure to Paclitaxel The functional propensity of residual tumour cells post therapy is never evaluated in conventional animal experimentation that accepts reduction in tumour volume as a qualifying endpoint to identify potential drug candidates. Such incomplete evaluation often remains a major reason for drug failure during clinical scale-up. The present example demonstrates an application embodied by the invention towards prediction of paclitaxel therapy (Sigma; i.p; 25 mg/kg body weight) outcomes under a specific regime (FIG. 7a), through modulation of tumour heterogeneity vis-à-vis different subpopulations that can be assigned specific functionalities. Generation of A4 serous ovarian adenocarcinoma xenografts, TDSCS, data acquisition and analysis to identify 18 discrete tumor cell populations is as detailed earlier. Administration of paclitaxel resulted in 50% reduction in tumor volumes at the end of the regime, most of which is through a decreased $PKH^{neg}$ fraction (FIG. 8b). Increased frequency of aneuploid progenitor cells following treatment suggests emergence of genetic instability that could further lead to drug resistance. An enhanced $PKH^{hi}$ (CSC) fraction is evident, and on further resolution revealed presence of cycling populations that have undergone less than 3-4 doublings within the $PKH^{hi}$ fraction (FIG. 8b inset). These suggest that CSCs have been shaken out of their dormancy to enter a cycling state towards regeneration following paclitaxel therapy. Regeneration of a drug refractory tumor is thus imminent and can be attributed to—(i) expansion of drug resistant euploid CSC clones (P18a-P18d) and (ii)

establishment of a parallel aneuploid regenerative hierarchy from emerging aneuploid CSC clones (P18a-P18d) that may provide diverse drug resistance mechanisms through random genetic rearrangements.

The present example highlights the limitations of consideration of either tumor volume reduction as an endpoint or alternatively, simple reductionist, individual analysis of the CSC hierarchies, DNA content or cell cycle based populations. Such systematic elucidation made possible by the present invention thereby presents an operational definition of functional tumour heterogeneity, which may be established as a benchmark in the drug discovery pipeline for evaluating responses of any new drug for its chemotherapeutic application over modulation of CSC hierarchies, genetic instability and differential cell cycle poise.

Example 4

Formulation of Improved Drug Combinations Including Possibilities of Drug Repositioning The methods of Example 3 can be applied for screening novel drug candidate(s) through specific cell target identification and/or re-evaluation of current drugs since such information is hitherto unavailable. This is an important value addition in understanding emerging resistance mechanisms besides enabling design of new drug combinations based on complementation of cell targeting efficacies. In the present example, the present inventors demonstrate such an application embodied by the invention through—(i) initial identification of drug sensitive and resistant tumour populations in response to paclitaxel, gemcitabine, 5AzadC, and a new, uncharacterized mouse monoclonal antibody (mAbX) and (ii) cell target based complementation to evolve efficient drug combinations.

The common responses to each individual drug tested either in short- or long-term treatments was—(i) significant reduction in tumour volumes and (ii) CSC re-entry into the cell cycle that suggests capability of regenerating a drug refractory state (FIG. 9). As seen in the grid representing responses to the individual treatments, gemcitabine appeared to be effective in short-term sensitization of all populations within the PKH$^{neg}$ fraction, 5 AzadC was effective against aneuploid fractions while mAbX sensitizes some of the cycling progenitor cells as well as quiescent CSCs. Thereby, a design of these three drugs in combination was purported to be most efficient and evaluated as a long-term regime. This indeed led to maximal tumour reduction (>80%) with cell composition of residual tumors indicating growth arrested populations.

The invention when applied with the above approaches is invaluable in combinationatorial drug repurposing and repositioning for design of efficacious therapeutic regimes.

The invention claimed is:

1. A method for evaluating cellular heterogeneity in tumours, wherein said method comprises the steps of:
    (i) obtaining a sample of tumour-derived single cell suspension, wherein said sample is from established cell lines or primary tumor samples;
    (ii) optionally fixing and permeabilizing said tumour-derived single cell suspension;
    (iii) combinatorial staining or labelling said tumour-derived single cell suspension with a binding dye, a fluorophore and/or antibodies specific to a marker on or in the tumour cells;
    (iv) concurrently and simultaneously resolving each cell in said labelled tumour-derived single cell suspension through multivariant flow cytometry or fluorescence activated cell sorting to three levels of resolution of its cellular components involving tumour proliferative or regenerative hierarchy, DNA content, and cell cycle phase;
    (v) detecting the frequency and identifying the profile of said levels of resolution of the tumour-derived single cell suspension; and
    (vi) subjecting said frequency and profile detected in step (v) to combinatorial analyses, wherein the first level of resolution is based on tumour proliferative or regenerative hierarchy; the second level is based on varying DNA content; and the third level is based on cell cycle phases.

2. The method as claimed in claim 1, wherein the binding dyes, fluorophores and/or antibodies are selected from the group consisting of vital membrane fluorophore dye, DNA binding dyes, RNA binding dyes, and antibodies that recognize a marker expressed in G1 but not G0 cell cycle phases, antibodies recognizing a marker expressed by G2M cell cycle phase.

3. The method as claimed in claim 1, wherein the combinatorial analyses identify at least two cellular subpopulations based on tumor regenerative hierarchy, DNA content and basic cell cycle phases.

4. The method as claimed in claim 3, wherein said at least two cellular subpopulations comprise one or more host cells selected from the group consisting of VMF$^{neg}$ Euploid G0, VFM$^{neg}$ Euploid G1, VFM$^{neg}$ Euploid S, VFM$^{neg}$ Euploid G2/M, VMF$^{neg}$ Aneuploid G0, VFM$^{neg}$ Aneuploid G1, VMF$^{neg}$ Aneuploid S, VFM$^{neg}$ Aneuploid G2/M, VMF$^{lo}$ Euploid G0, VMF$^{lo}$ Euploid G1, VMF$^{lo}$ Euploid S, VMF$^{lo}$ Euploid G2/M, VMF$^{lo}$ Aneuploid G0, VMF$^{lo}$ Aneuploid G1, VMF$^{lo}$ Aneuploid S, VMF$^{lo}$ Aneuploid G2/M, VMF$^{hi}$ Euploid G0, VMF$^{hi}$ Euploid G1, VMF$^{hi}$ Euploid S, VMF$^{hi}$ Euploid G2/M, VMF$^{hi}$ Aneuploid G0, VMF$^{hi}$ Aneuploid G1, VMF$^{hi}$ Aneuploid S, and VMF$^{hi}$ Aneuploid G2/M.

5. The method as claimed in claim 1, further comprising the step of screening molecules having therapeutic potential, wherein said method is based on the cell subpopulation specific responses to drugs, either individually or in combination employing the method of claim 3.

6. The method as claimed in claim 1, further comprising the step of drug repositioning, wherein said method is based on the cell subpopulation specific responses to drugs either individually or in combination employing the method of claim 3.

7. A method for monitoring tumour cell populations, which method employs the steps of:
    (i) obtaining a sample of tumour-derived single cell suspension, wherein said sample is from established cell lines or primary tumor samples;
    (ii) optionally fixing and permeabilizing said tumour-derived single cell suspension;
    (iii) combinatorial staining or labelling said tumour-derived single cell suspension with a binding dye, a fluorophore and/or antibodies specific to a marker on or in the tumour cells;
    (iv) concurrently and simultaneously resolving each cell in said labelled tumour-derived single cell suspension through multivariant flow cytometry or fluorescence activated cell sorting to three levels of resolution of its cellular components involving tumour proliferative or regenerative hierarchy, DNA content, and cell cycle phase;
    (v) detecting the frequency and identifying the profile of said levels of resolution of the tumour-derived single cell suspension; and (vi) subjecting said frequency and profile detected in step (v) to combinatorial analyses, wherein the first level of resolution is based on tumour proliferative or regenerative hierarchy; the second level is based on varying DNA content; and the third level is based on cell cycle phases.

* * * * *